US00RE46071E

(19) United States
(12) Reissued Patent
MacCallum

(10) Patent Number: US RE46,071 E
(45) Date of Reissued Patent: Jul. 19, 2016

(54) GAS RECONDITIONING SYSTEMS

(71) Applicant: PARAGON SPACE DEVELOPMENT CORPORATION, Tucson, AZ (US)

(72) Inventor: Taber K. MacCallum, Tucson, AZ (US)

(73) Assignee: Paragon Space Development Corporation, Tucson, AZ (US)

(21) Appl. No.: 14/694,065

(22) Filed: Apr. 23, 2015

Related U.S. Patent Documents

Reissue of:
(64) Patent No.: 8,424,515
Issued: Apr. 23, 2013
Appl. No.: 12/367,421
Filed: Feb. 6, 2009

U.S. Applications:
(60) Provisional application No. 61/026,841, filed on Feb. 7, 2008.

(51) Int. Cl.

| | |
|---|---|
| ***A62B 17/04*** | (2006.01) |
| ***A62B 17/00*** | (2006.01) |
| ***A62B 18/08*** | (2006.01) |
| ***F24F 5/00*** | (2006.01) |
| ***F24J 3/00*** | (2006.01) |
| ***B64G 6/00*** | (2006.01) |
| ***B64G 1/48*** | (2006.01) |
| ***A61M 16/10*** | (2006.01) |
| ***F28D 21/00*** | (2006.01) |

(Continued)

(52) U.S. Cl.
CPC ..... *B64G 6/00* (2013.01); *A61M 16/1045* (2013.01); *A61M 16/1075* (2013.01); *B63C 11/24* (2013.01); *B64G 1/48* (2013.01); *F24F 5/0007* (2013.01); *F24F 5/0096* (2013.01); *F28D 21/0001* (2013.01); *A61M 16/22* (2013.01); *A61M 2205/3606* (2013.01)

(58) Field of Classification Search
CPC ..... B64G 6/00; B64G 1/48; F28D 21/0001; A61M 16/1045; A61M 16/1075; A61M 2205/3606; A61M 16/22; B63C 11/24; F24F 5/007; F24F 5/0096
USPC ..... 128/201.22, 201.29, 202.11, 201.13, 128/204.15, 204.16, 204.17
See application file for complete search history.

(56) References Cited

U.S. PATENT DOCUMENTS 4,005,708 A * 2/1977 Netteland et al. ..... 128/205.28
4,168,706 A * 9/1979 Fletcher et al. ..... A62B 7/10 128/204.16
4,238,211 A * 12/1980 Stuart ..... 62/639

(Continued)

OTHER PUBLICATIONS

Jones, Eric M. & Glover, Ken (eds); Apollo Lunar Surface Journal: ECS Functional Description—Atmosphere Revitalization Section; Internet web site available at hitp://www.hq.nasa.gov/alsj/alsj-ECSFunDesARS.html; publication date unknown (Internet web site last revised Oct. 13, 2008).

(Continued)

*Primary Examiner* — William Doerrler
(74) *Attorney, Agent, or Firm* — Weaver Austin Villeneuve & Sampson, LLP

(57) ABSTRACT

Closed system breathable gas regeneration systems comprising temperature swing adsorption ("TSA") using metabolic regeneration, such systems being useful for EVA in extraterrestrial environments having hostile atmospheres.

49 Claims, 9 Drawing Sheets

(51) Int. Cl.

| | |
|---|---|
| ***B63C 11/24*** | (2006.01) |
| *A61M 16/22* | (2006.01) |

(56) References Cited

U.S. PATENT DOCUMENTS

| | | | | | |
|---|---|---|---|---|---|
| 4,409,978 | A * | 10/1983 | Bartos | 128/205.12 | |
| 4,428,372 | A * | 1/1984 | Beysel et al. | 128/202.26 | |
| 4,661,133 | A * | 4/1987 | Lavie | 62/636 | |
| 4,738,119 | A * | 4/1988 | Zafred | A41D 13/0053 2/81 | |
| 4,781,184 | A * | 11/1988 | Fife | 128/205.12 | |
| 5,111,809 | A * | 5/1992 | Gamble et al. | 128/204.18 | |
| 5,143,060 | A * | 9/1992 | Smith | 128/205.28 | |
| 5,398,675 | A * | 3/1995 | Henkin et al. | 128/203.12 | |
| 5,438,978 | A * | 8/1995 | Hardester, III | 128/201.13 | |
| 5,487,380 | A * | 1/1996 | Grabenkort | 128/204.15 | |
| 5,740,682 | A * | 4/1998 | Lavie | 62/617 | |
| 5,964,221 | A * | 10/1999 | McKenna | 128/205.12 | |
| 5,992,413 | A * | 11/1999 | Martin et al. | 128/201.13 | |
| 6,041,777 | A * | 3/2000 | Faithfull et al. | 128/200.24 | |
| 6,123,674 | A * | 9/2000 | Rich | 600/529 | |
| 6,200,271 | B1 * | 3/2001 | Kuck et al. | 600/532 | |
| 6,210,342 | B1 * | 4/2001 | Kuck et al. | 600/504 | |
| 6,363,930 | B1 * | 4/2002 | Clawson et al. | 128/201.13 | |
| 6,523,538 | B1 * | 2/2003 | Wikefeldt | 128/204.18 | |
| 6,575,164 | B1 * | 6/2003 | Jaffe et al. | 128/205.24 | |
| 6,631,717 | B1 * | 10/2003 | Rich et al. | 128/205.13 | |
| 7,329,307 | B2 * | 2/2008 | Hrycak et al. | 95/139 | |
| 7,520,280 | B2 * | 4/2009 | Gordon | 128/205.28 | |
| 7,634,998 | B1 * | 12/2009 | Fenley | 128/201.13 | |
| 7,674,281 | B2 * | 3/2010 | Worm | A62B 17/005 128/201.29 | |
| 7,698,905 | B1 * | 4/2010 | Carpenter | A61F 7/02 62/259.3 | |
| 7,814,908 | B2 * | 10/2010 | Psaros | 128/205.28 | |
| 7,922,789 | B1 * | 4/2011 | Deane et al. | 95/96 | |
| 2002/0148471 | A1 * | 10/2002 | Hirabayashi | 128/205.12 | |
| 2003/0150232 | A1 * | 8/2003 | Brudnicki | A62B 7/06 62/259.3 | |
| 2007/0100250 | A1 * | 5/2007 | Kline | 600/532 | |
| 2007/0163591 | A1 * | 7/2007 | Ross et al. | 128/205.12 | |
| 2007/0250050 | A1 * | 10/2007 | Lafontaine | 606/21 | |
| 2008/0221471 | A1 * | 9/2008 | Djupesland et al. | 600/543 | |
| 2009/0032023 | A1 * | 2/2009 | Pastre et al. | 128/205.28 | |
| 2009/0038615 | A1 * | 2/2009 | Bradley | 128/204.17 | |
| 2009/0120432 | A1 * | 5/2009 | MacDonald et al. | 128/201.13 | |
| 2010/0037893 | A1 * | 2/2010 | Grilliot et al. | 128/202.19 | |
| 2010/0077795 | A1 * | 4/2010 | Shah et al. | 62/619 | |
| 2010/0078027 | A1 * | 4/2010 | Ogasahara | 128/205.12 | |
| 2010/0212668 | A1 * | 8/2010 | Flanagan et al. | 128/203.16 | |
| 2010/0252034 | A1 * | 10/2010 | Ross et al. | 128/202.26 | |
| 2011/0061361 | A1 * | 3/2011 | Shah et al. | 60/39.12 | |
| 2011/0209707 | A1 * | 9/2011 | Terhark | 128/205.11 | |

OTHER PUBLICATIONS

Christine Iacomini, Aaron Powers, Chad Bower, Katherine Straub-Lopez, Grant Anderson, and Taber MacCallum and Heather L. Paul; Metabolic heat regenerated Temperature Swing Adsorption for CO2 & Heat Removal/Rejection in a Martian PLSS; 07ICES-243 (likely May 29, 2007, but unable to confirm publication date), available at http://ntrs.nasa.gov/archive/nasa/casi.ntrs.nasa.gov/20070016701_2007014444.pdf (Internet web site last visited Feb. 6, 2009).

National Aeronautics and Space Administration, Metabolic Heat Regenerated Temperature Swing Adsorption for CO2 and Heat Removal/Rejection in a Martian PLSS, Scientific and Technical Aerospace Reports, May 29, 2007, p. 117, vol. 45, No. 10, published by NASA, available at http://202.118.250.135/nasa/STAR/star0710.pdf (Internet web site last visited Feb. 6, 2009).

* cited by examiner

GAS RECONDITIONING SYSTEMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

The present application is related to and claims priority from prior provisional application Ser. No. 61/026,841, filed Feb. 7, 2008, entitled "Metabolic heat regenerated Temperature Swing Adsorption (MTSA)", the contents of which are incorporated herein by this reference and are not admitted to be prior art with respect to the present invention by the mention in this cross-reference section.

STATEMENT REGARDING FEDERALLY SPONSORED RESEARCH OR DEVELOPMENT

Some embodiments of this invention were developed with United States Government support under NNJO6HA98C awarded by The National Aeronautics and Space Administration. The Government may have certain rights in the invention.

BACKGROUND

This invention relates to providing a system for improved gas reconditioning relating to human respiration. More particularly this invention relates to providing a system for reconditioning cycled air in contained environments. In hostile environments, such as in space or on celestial bodies without a breathable atmosphere, it is required to provide a contained space in which a person may receive life support.

In highly remote hostile environments, it is desirable to use a regeneratable gas reconditioning system rather than a non-regeneratable consumable gas reconditioning system. Consumables are difficult to replace, and add to the weight that must be launched from Earth, increasing expense. However, any regeneratable gas reconditioning system also uses materials and energy in the regeneration process, which also add weight and expense when launched from Earth. Therefore, a gas reconditioning system is needed that is regeneratable and consumes less materials required to be launched from Earth.

OBJECTS AND FEATURES OF THE INVENTION

A primary object and feature of the present invention is to provide a gas reconditioning system overcoming the above-mentioned problem.

It is a further object and feature of the present invention to provide such a gas reconditioning system that is regeneratable.

Another primary object and feature of the present invention is to provide such a gas reconditioning system that ejects only waste materials native to the remote hostile environment.

It is a further object and feature of the present invention to provide such a gas reconditioning system that recycles heat.

It is another object and feature of the present invention to provide such a gas reconditioning system that recycles water.

Another primary object and feature of the present invention is to provide such a gas reconditioning system, which in it regeneration cycle, uses materials readily available in a remote hostile environment.

It is a further object and feature of the present invention to provide such a gas reconditioning system that operates using less consumable materials launched from Earth.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a system, relating to human respiration in extraterrestrial environments, comprising: at least one expiration-breath holder adapted to hold expired breath; at least one expiration-breath cooler adapted to cool the expired breath; at least one gas-impermeable separator adapted to separate such at least one expiration-breath holder from such at least one expiration-breath cooler; at least one thermal conductor adapted to assist thermal conductivity between such expired breath and such at least one expiration-breath cooler; and wherein such at least one expiration-breath holder comprises at least one moisture capturer adapted to capture moisture from such expired breath as such expired breath is cooled by such at least one expiration-breath cooler, assisting formation of cooled, de-humidified expired breath; at least one moisture holder adapted to hold moisture captured by such at least one moisture capturer; at least one inspiration-breath holder adapted to hold portions of such expired breath desired to be included in inspiration breath; at least one inspiration-breath warmer adapted to warm such portions of such expired breath prior to inspiration; and at least one re-humidifier adapted to re-humidify such portions of such expired breath; Wherein such at least one re-humidifier comprises at least one moisture returner adapted to return the captured moisture from such at least one moisture capture to such portions of such expired breath, assisting formation of warmed humidified such portions to include in such inspiration breath.

Moreover, it provides such a system wherein such at least one expiration-breath cooler comprises such cooled, de-humidified expired breath. Additionally, it provides such a system further comprising: at least one breathable gas storer adapted to store breathable gas; and at least one breathable gas mixer adapted to mix breathable gas from such at least one breathable gas storer with such warmed humidified portions.

Also, it provides such a system further comprising at least one carbon dioxide adsorber adapted to adsorb carbon dioxide from such cooled, de-humidified expired breath. Additionally, it provides such a system wherein such at least one carbon dioxide adsorber comprises at least one sorbent adapted to adsorb and/or desorb carbon dioxide, the mode correlating with temperature of such at least one sorbent. In addition, it provides such a system wherein such at least one sorbent comprises at least one desorber adapted to desorbing carbon dioxide into the environment to re-prepare such at least one sorbent for re-use as such carbon dioxide adsorber. And, it provides such a system wherein such desorber uses thermal transfer from warmth of such expired breath to attain at least one desorbing condition.

Further, it provides such a system further comprising at least one further cooler adapted to further cool such cooled, de-humidified expired breath. Even further, it provides such a system wherein such at least one further cooler comprises liquid carbon dioxide. Moreover, it provides such a system wherein such liquid carbon dioxide comprises such at least one carbon dioxide adsorber.

Additionally, it provides such a system further comprising: at least one extraterrestrial body suit adapted to extraterrestrial body protection; and at least one suit cooler adapted to cool body-heat suit warming; wherein such at least one suit cooler comprises such liquid carbon dioxide.

In accordance with another preferred embodiment hereof, this invention provides a method, relating to human respiration in extraterrestrial environments, comprising the steps of: collecting and holding expired breath; cooling such expired breath using at least one expired-breath cooler; gas-impermeably separating such expired breath from such at least one expired-breath cooler; assisting thermal conductivity between such expired breath and such at least one expired-breath cooler; capturing moisture from such expired breath as such expired breath is cooled by such at least one expired-breath cooler, assisting formation of cooled, de-humidified expired breath; holding such captured moisture; holding portions of such expired breath desired to be included in inspiration breath; warming such portions of such expired breath prior to inspiration; and re-humidifying, with such captured moisture, such portions of such expired breath to form warmed humidified such portions to include in such inspiration breath.

Also, it provides such a method wherein such at least one expired-breath cooler comprises such cooled, de-humidified expired breath. In addition, it provides such a method further comprising the steps of: storing breathable gas; and mixing such breathable gas with such warmed humidified portions prior to inspiration. And, it provides such a method further comprising adsorbing carbon dioxide from such cooled, de-humidified expired breath. Additionally, it provides such a method wherein such adsorbing utilizes at least one sorbent adapted to adsorb and/or desorb carbon dioxide, the mode correlating with temperature of such at least one sorbent.

Further, it provides such a method further comprising desorbing carbon dioxide into the environment to re-prepare such at least one sorbent for re-use in such adsorbing. Even further, it provides such a method Wherein such desorbing utilizes thermal transfer from warmth of such expired breath to attain at least one desorbing condition. Moreover, it provides such a method further comprising further cooling such cooled, de-humidified expired breath. Additionally, it provides such a method wherein such further cooling utilizes liquid carbon dioxide. Also, it provides such a method wherein such adsorbing utilizes such liquid carbon dioxide. In addition, it provides such a method further comprising protecting at least one body in at least one extraterrestrial suit; and cooling body-heat warming such at least one extraterrestrial suit; wherein such cooling utilizes such liquid carbon dioxide.

In accordance with another preferred embodiment hereof, this invention provides a system, relating to human respiration in extraterrestrial environments, comprising: expiration-breath holder means for holding expired breath; expiration-breath cooler means for cooling the expired breath; gas-impermeable separation means for separating such expiration-breath holder means from such expiration-breath cooler means; thermal conductor means for assisting thermal conductivity between such expired breath and such expiration-breath cooler means; wherein such expiration-breath holder means comprises moisture capturer means for capturing moisture from such expired breath as such expired breath is cooled by such expiration-breath cooler means, assisting formation of cooled, de-humidified expired breath; moisture holder means for holding moisture captured by such moisture capturer means; inspiration-breath holder means for holding portions of such expired breath desired to be included in inspiration breath; inspiration-breath warming means for warming such portions of such expired breath prior to inspiration; and re-humidifier means for re-humidifying such portions of such expired breath; wherein such re-humidifier means comprises moisture returning means for returning the captured moisture from such moisture capturer means to such portions of such expired breath to form warmed, humidified such portions for inclusion in such inspiration breath.

And, it provides such a system wherein such expiration-breath cooler means comprises such cooled, de-humidified expired breath. Further, it provides such a system further comprising: breathable gas storage means for storing breathable gas; and breathable gas mixing means for mixing breathable gas from such breathable gas storage means with such warmed, humidified portions.

Even further, it provides such a system further comprising carbon dioxide adsorber means for adsorbing carbon dioxide from such cooled, de-humidified expired breath. Additionally, it provides such a system wherein such carbon dioxide adsorber means comprises sorbent means for adsorbing and/or desorbing carbon dioxide, the mode correlating with sorbent temperature. Even further, it provides such a system wherein such sorbent means comprises desorber means for desorbing carbon dioxide into the environment to re-prepare such sorbent means for re-use as such adsorber means. Even further, it provides such a system wherein such desorber means uses thermal transfer from warmth of such expired breath to attain at least one desorbing condition.

Even further, it provides such a system further comprising further cooling means for further cooling such cooled, de-humidified expired breath. Even further, it provides such a system wherein such further cooling means comprises liquid carbon dioxide. Even further, it provides such a system wherein such liquid carbon dioxide comprises such carbon dioxide adsorber means. Even further, it provides such a system further comprising: extraterrestrial body suit means for extraterrestrial body protection; and suit cooling means for cooling body-heat suit warming; wherein such suit cooling means comprises such liquid carbon dioxide.

And it provides for each and every novel feature, element, combination, step and/or method disclosed or suggested herein.

DETAILED DESCRIPTION OF THE BEST MODES AND PREFERRED EMBODIMENTS OF THE INVENTION

Figure 1:
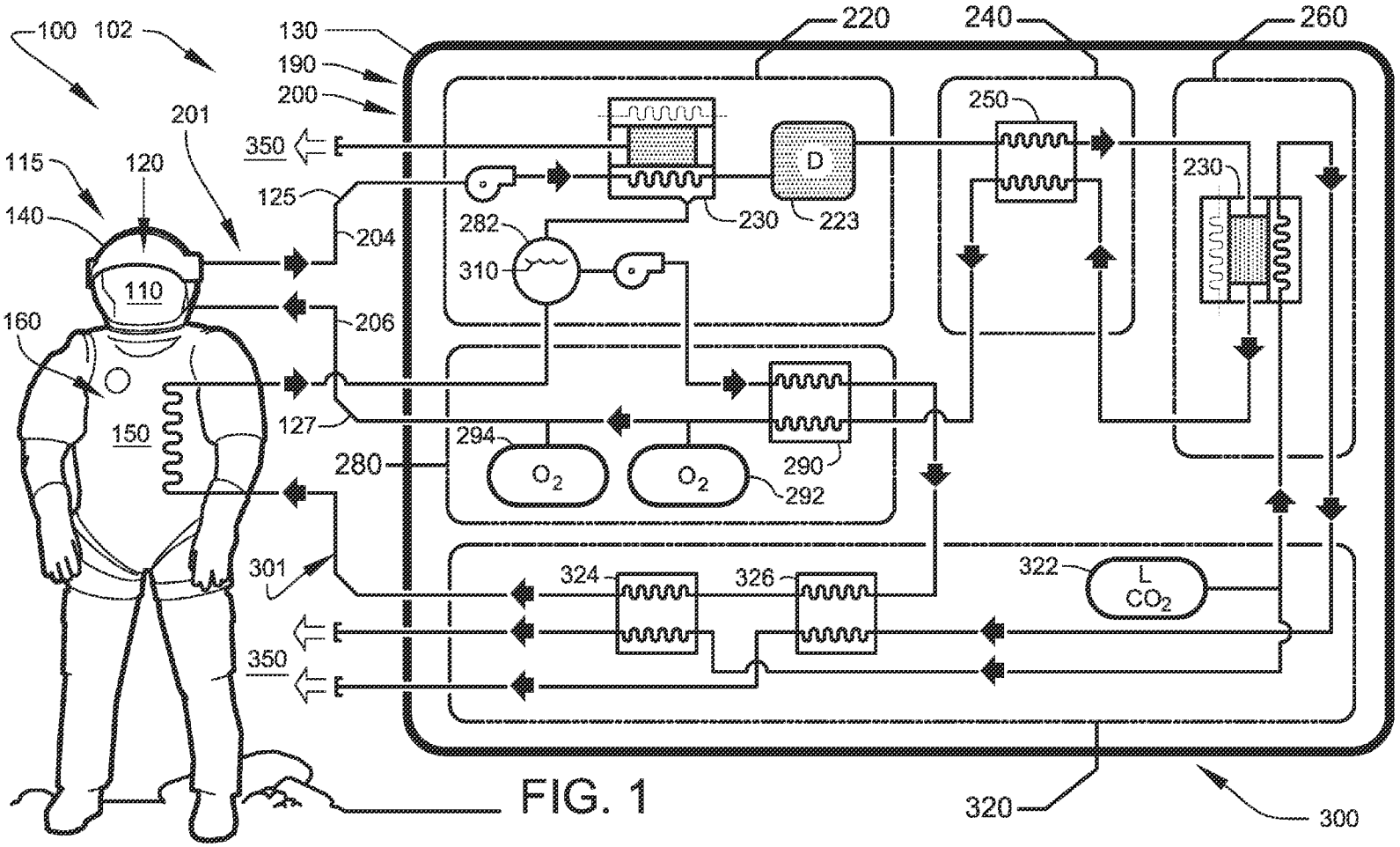
FIG. 1 shows a diagrammatic view, illustrating at least one environmental conditioning cycle of at least one contained environment in at least one gas reconditioning system, according to a preferred embodiment of the present invention.

FIG. 1 shows a diagrammatic view, illustrating at least one environmental conditioning cycle 190 of at least one contained environment 110 in at least one gas reconditioning system 100, according to a preferred embodiment of the present invention. Gas reconditioning system 100 preferably reconditions respirated gases 125 contained in contained environment 110, as shown.

Gas reconditioning system 100 preferably comprises embodiment 102, as shown. In embodiment 102, contained environment 110 preferably comprises, as shown, conditioned liquid cooling and ventilation garment 115 and preferably at least one conditioning pack 130, preferably portable. Upon reading the teachings of this specification, those skilled in the art will now appreciate that, under appropriate circumstances, considering such issues as future technology, cost, environmental limitations, etc., other contained environments, such as, for example, habitation modules, vehicles, etc., may suffice.

Liquid cooling and ventilation garment 115 preferably comprises, as shown, at least one respiration chamber 120, preferably at least one helmet 140, preferably designed to contain gases for the purpose of respiration. Respirated gases 125 are preferably collected and preferably reconditioned into reconditioned gases 127 in respiration conditioning cycle 200, as shown.

Liquid cooling and ventilation garment 115 preferably further comprises at least one thermally regulated chamber 150, preferably comprising at least one bodysuit 160 (at least embodying herein at least one extraterrestrial body suit adapted to extraterrestrial body protection; and at least embodying herein protecting at least one body in at least one extraterrestrial suit), as shown. Thermally regulated chamber 150 preferably comprises at least one thermal conditioning cycle 300, as shown, preferably circulating at least one thermal conditioning fluid 310.

Respiration conditioning cycle 200 preferably comprises at least one respiration-conditioning loop 201. Thermal conditioning cycle 300 preferably comprises at least one thermal conditioning loop 301. Respiration conditioning loop 201 and thermal conditioning loop 301 are preferably contained within conditioning pack 130. Conditioning pack 130 is preferably sized appropriate to contained environment 110. In embodiment 102, conditioning pack 130 preferably sized to be carried on liquid cooling and ventilation garment 115, as shown.

Respiration conditioning cycle 200 preferably comprises, as shown, at least one water extraction stage 220, at least one heat recuperation stage 240, at least one gas scrubbing stage 260, at least one resupply stage 280, and at least one coolant use process 320. Additionally, thermal conditioning cycle 300 preferably utilizes coolant use process 320 and preferably is utilized by resupply stage 280, as shown.

Respiration conditioning loop 201 receives respirated gases 125 from respirations chamber 120 through respiration exhaust 204 (at least embodying herein at least one expiration-breath holder adapted to hold expired breath; and at least embodying herein collecting and holding expired breath; and at least embodying herein expiration-breath holder means for holding expired breath). After passing through respiration conditioning loop 201 and undergoing each stage of respiration conditioning cycle 200, reconditioned gases 127 preferably returns from respiration conditioning loop 201 through return line 206 (at least embodying herein at least one inspiration-breath holder adapted to hold portions of such expired breath desired to be included in inspiration breath; and at least embodying herein holding portions of such expired breath desired to be included in inspiration breath; and at least embodying herein inspiration-breath holder means for holding portions of such expired breath desired to be included in inspiration breath).

Embodiment 102 is preferably used, as shown, in at least one external environment 350 comprising at least one carbon-dioxide-rich environment, preferably Mars. Upon reading the teachings of this specification, those skilled in the art will now appreciate that, under appropriate circumstances, considering such issues as future technology, cost, manned-space flight reach, etc., other external environments, such as, for example, Io, Earth's Moon, an asteroid, space, other carbon-dioxide-rich environments, etc., may suffice.

Figure 2:
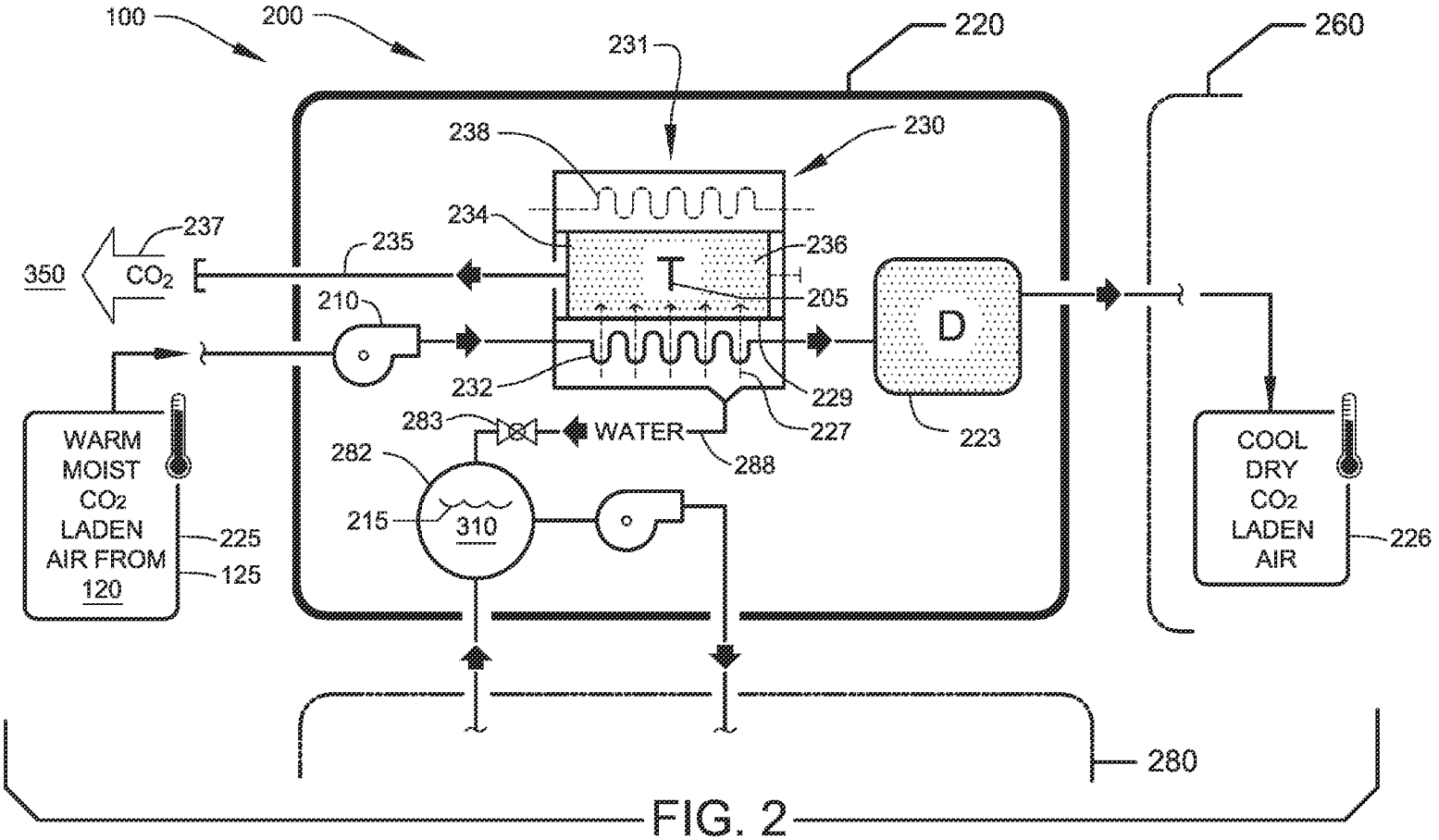
FIG. 2 shows a diagrammatic view, illustrating at least one water extraction stage of at least one respiration conditioning cycle, according to the preferred embodiment of FIG. 1.

FIG. 2 shows a diagrammatic view, illustrating water extraction stage 220 of respiration conditioning cycle 200, according to the preferred embodiment of FIG. 1.

At least one air bearing fan 210 preferably circulates gases through respiration conditioning loop 201, as shown. Upon reading the teachings of this specification, those skilled in the art will now appreciate that, under appropriate circumstances, considering such issues as future technologies, pressure variations, costs, etc., other gas circulators, such as, for example, pumps, movement assisted valves, other fans, etc., may suffice.

At least one metabolic heat regenerated temperature swing adsorption module 230 (MTSA module) preferably comprises, as shown, at least one sorbent-bed chamber 234, at least one heat exchanger 232 and at least one heat exchanger 238. Sorbent-bed chamber 234 preferably contains at least one sorbent bed 236.

Figure 4:
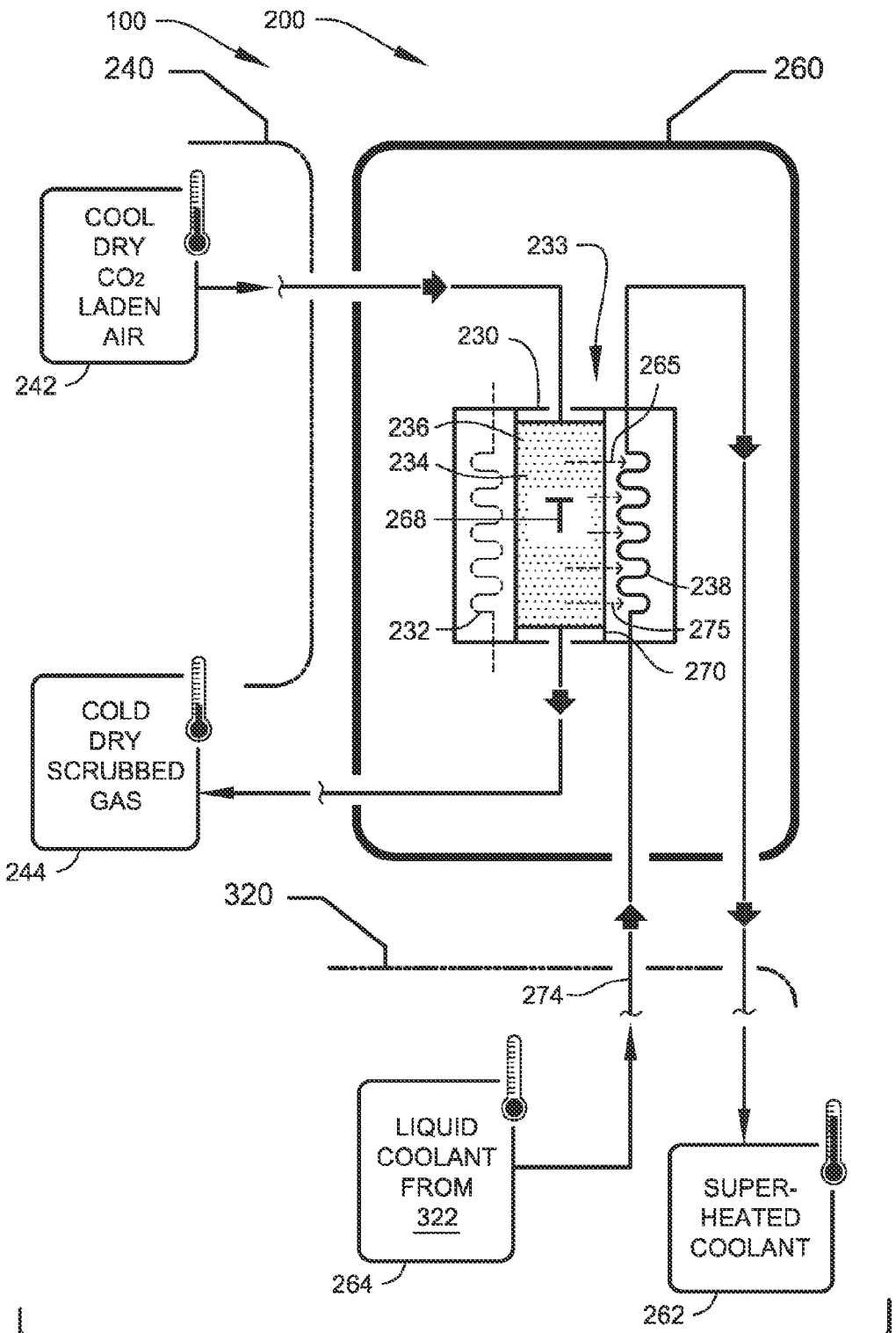
FIG. 4 shows a diagrammatic view, illustrating at least one gas scrubbing stage of the respiration conditioning cycle, according to the preferred embodiment of FIG. 1.

Further, metabolic heat regenerated temperature swing adsorption module 230 preferably comprises at least two modes of operation, preferably desorption mode, denoted as desorbing MTSA module 231, as shown and preferably adsorption mode, denoted as adsorbing MTSA module 233 (see FIG. 4). At least two metabolic heat regenerated temperature swing adsorption modules 230 are required for continuous operation (see discussion of FIG. 7A and FIG. 7B), one desorbing MTSA module 231, and one adsorbing MTSA module 233.

Respirated gases 125 are passed to desorbing MTSA module 231, as shown. Sorbent bed 236 (at least herein embodying wherein such at least one sorbent comprises at least one desorber adapted to desorbing carbon dioxide into the environment to re-prepare such at least one sorbent for re-use as such carbon dioxide adsorber) in desorbing MTSA module 231 releases quantities of carbon dioxide gas 237, as shown. Further discussion of metabolic heat regenerated temperature swing adsorption module 230 may be found in FIGS. 7A through 9.

Respirated gases 125 from respiration chamber 120 comprise warm moist carbon-dioxide-laden gases 225, as shown. Warm moist carbon-dioxide-laden gases 225 preferably warm sorbent bed 236 in desorbing MTSA module 231 (at least embodying herein at least one expiration-breath cooler adapted to cool the expired breath; and at least embodying herein cooling such expired breath using at least one expired-breath cooler; and at least embodying herein expiration-breath cooler means for cooling the expired breath), preferably to desorption temperature 205, preferably via heat exchanger 232 using heat exchange 227, as shown. Heat exchanger 232 preferably comprises, as shown, at least one condensing heat exchanger, preferably at least one condensing ice heat exchanger. Heat exchange 227 preferably occurs through at least one gas impermeable barrier 229 (at least embodying herein at least one gas-impermeable separator adapted to separate such at least one expiration-breath holder from such at least one expiration-breath cooler; and at least embodying herein gas-impermeable separation means for separating such expiration-breath holder means from such expiration-breath cooler means; and at least embodying herein gas-impermeably separating such expired breath from such at least one expired-breath cooler), as shown. Upon reading the teachings of this specification, those skilled in the art will now appreciate that, under appropriate circumstances, considering such issues as future technology, cost, operation temperatures, etc., other heat exchangers may suffice.

Heat exchange 227 preferably causes desorption, from sorbent bed 236, of carbon dioxide gas 237, as shown. Carbon dioxide gas 237 is preferably removed from respiration conditioning cycle 200, preferably released to external environment 350 through at least one exhaust 235 (at least embodying herein desorbing carbon dioxide into the environment to re-prepare such at least one sorbent for re-use in such adsorbing), as shown. Upon reading the teachings of this specification, those skilled in the art will now appreciate that, under appropriate circumstances, considering such issues as future technology, cost, environment conditions, etc., other carbon dioxide removal methods, such as, for example, storage, sequestration, etc., may suffice.

Heat exchange 227 preferably comprises transfer of heat from particles of warm moist carbon-dioxide-laden gases 225. Further, heat exchange 227 preferably comprises transfer of heat front water condensation out of warm moist carbon-dioxide-laden gases 225, as shown. Heat exchange 227 (at least herein embodying wherein such desorber uses thermal transfer from warmth of such expired breath to attain at least one desorbing condition; and at least herein embodying wherein such desorbing utilizes thermal transfer from warmth of such expired breath to attain at least one desorbing condition) preferably transfers heat required to desorb carbon dioxide gas 237, as shown, cooling warm moist carbon-dioxide-laden gases 225.

Water condensation from warm moist carbon-dioxide-laden gases 225 initially forms ice in heat exchanger 232 (at least embodying herein capturing moisture from such expired breath as such expired breath is cooled by such at least one expired-breath cooler, assisting formation of cooled, de-humidified expired breath; and at least herein embodying wherein such at least one expiration-breath holder comprises at least one moisture capturer adapted to capture moisture from such expired breath as such expired breath is cooled by such at least one expiration-breath cooler, assisting formation of cooled, de-humidified expired breath; and at least herein embodying wherein such expiration-breath holder means comprises moisture capturer means for capturing moisture from such expired breath as such expired breath is cooled by such expiration-breath cooler means, assisting formation of cooled, de-humidified expired breath), during heat exchange 227. Once sorbent bed 236 reaches desorption temperature 205 (see FIG. 7A), the ice preferably melts forming water 215, as shown. Water 215 is preferably gravity fed, preferably through feed line 288. At least one feedwater accumulator 282 preferably collects water 215, as shown, preferably from feed line 288 through at least one check valve 283. Water 215 is preferably injected into thermal conditioning loop 301 (at least embodying herein at least one moisture holder adapted to hold moisture captured by such at least one moisture capturer; and at least embodying herein holding such captured moisture; and at least embodying herein moisture holder means for holding moisture captured by such moisture capturer means), as shown. Water 215 is preferably collected for later recycling. Upon reading the teachings of this specification, those skilled in the art will now appreciate that, under appropriate circumstances, considering such issues as future technology, cost, environmental limitations, etc., other water collectors, such as, for example, water-impermeable membranes, reversible chemical reactions, etc., may suffice.

Any remaining water vapor from warm moist carbon-dioxide-laden gases 225, not removed in heat exchanger 232, is preferably removed by at least one desiccant 223, as shown. Desiccant 223 preferably comprises at least one silica gel bed. Upon reading the teachings of this specification, those skilled in the art will now appreciate that, under appropriate circumstances, considering such issues as future technology, cost, system limitations, etc., other desiccants, such as, for example, aerogel, calcium sulfate, calcium chloride, montmorillonite clay, molecular sieves, etc., may suffice.

Passing through heat exchanger 232 and desiccant 223 preferably removes water vapor from and cools warm moist carbon-dioxide-laden gases 225 to form cooler dry carbon-dioxide-laden gases 226, as shown. Cooler dry carbon-dioxide-laden gases 226 then pass into heat recuperation stage 240, as shown.

Figure 3:
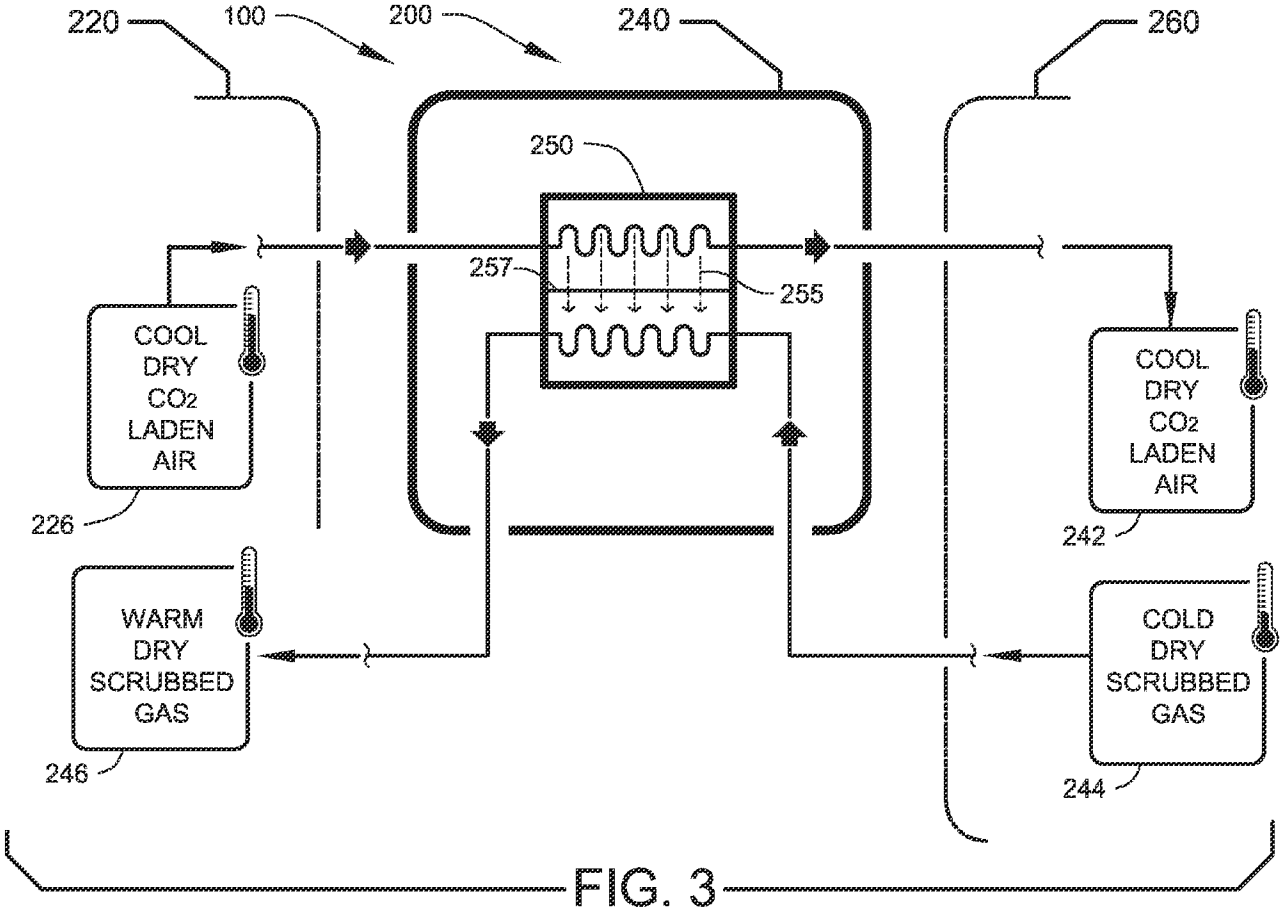
FIG. 3 shows a diagrammatic view, illustrating at least one recuperative heat stage of the respiration conditioning cycle, according to the preferred embodiment of FIG. 1.

FIG. 3 shows a diagrammatic view, illustrating heat recuperation stage 240 of respiration conditioning cycle 200, according to the preferred embodiment of FIG. 1. To conserve liquid coolant 264 (see FIG. 4), heat recuperation stage 240 preferably utilizes at least one recuperative heat exchange 255 in at least one recuperative heat exchanger 250, as shown.

Recuperative heat exchange 255 preferably exchanges heat across at least one gas impermeable barrier 257, as shown. Cooler dry carbon-dioxide-laden gases 226 preferably passes through recuperative heat exchanger 250, preferably surrendering, heat in recuperative heat exchange 255, becoming cool dry carbon-dioxide-laden gas 242. Cool dry carbon-dioxide-laden gas 242 preferably proceeds to gas scrubbing stage 260.

Cold dry scrubbed gas 244, returning from gas scrubbing stage 260, preferably passes through recuperative heat exchanger 250. Cold dry scrubbed gas 244 preferably gathers surrendered heat in recuperative heat exchange 255 becoming warmer dry scrubbed gas 246. Warmer dry scrubbed gas 246 preferably proceeds to resupply stage 280.

FIG. 4 shows a diagrammatic view, illustrating gas scrubbing stage 260 of respiration conditioning cycle 200, according to the preferred embodiment of FIG. 1. Gas scrubbing stage 260 preferably intakes cool dry carbon-dioxide-laden gas 242, preferably scrubs the carbon dioxide and preferably produces cold dry scrubbed gas 244, as shown. Gas scrubbing stage 260 uses sorbent bed 236 (at least embodying herein adsorbing carbon dioxide from such cooled, de-humidified expired breath; and at least embodying herein at least one carbon dioxide adsorber adapted to adsorb carbon dioxide from such cooled, de-humidified expired breath), in adsorbing MTSA module 233, at adsorption temperature 268 (see FIG. 7A) to trap carbon dioxide for later desorption as carbon dioxide gas 237.

Adsorbing MTSA module 233 preferably comprises at least one sublimation heat exchange 265 and preferably at least one coolant-superheating heat exchange 275, as shown. Sublimation heat exchange 265 preferably comprises liquid coolant 264 changing phase from liquid state to solid, preferably in isenthalpic expansion, then to vapor, preferably in isothermal sublimation. Coolant-superheating heat exchange 275 preferably superheats, preferably in isobaric warming, vapor resulting from sublimation heat exchange 265. Both sublimation heat exchange 265 and coolant-superheating heat exchange 275 preferably occur between heat exchanger 238 and sorbent-bed chamber 234 preferably across at least one gas impermeable barrier 270, as shown.

Cool dry carbon-dioxide-laden gas 242 preferably enters adsorbing MTSA module 233 (at least herein embodying wherein such liquid carbon dioxide comprises such at least one carbon dioxide adsorber; and at least herein embodying wherein such adsorbing utilizes such liquid carbon dioxide) and preferably transfers heat in coolant-superheating heat exchange 275, thereby cooling to adsorption temperature 268. As carbon dioxide adsorption occurs, heat is released and preferably removed from sorbent bed 236 in vaporizing heat exchange 265. Adsorption of carbon dioxide from cool dry carbon-dioxide-laden gas 242 and related cooling from coolant-superheating heat exchange 275 (at least embodying herein at least one further cooler adapted to further cool such cooled, de-humidified expired breath; and at least embodying herein further cooling such cooled, de-humidified expired breath) and sublimation heat exchange 265 produce cold dry scrubbed gas 244, as shown. Cold dry scrubbed gas 244 preferably feeds into heat recuperation stage 240, as shown, and is warmed as described in FIG. 3.

Liquid coolant 264 preferably feeds into heat exchanger 238, through liquid coolant line 274, from liquid coolant supply 322. Following sublimation heat exchange 265 and coolant-superheating heat exchange 275 (at least herein embodying wherein such at least one further cooler comprises liquid carbon dioxide; and at least herein embodying wherein such further cooling utilizes liquid carbon dioxide), liquid coolant 264 becomes superheated coolant 262, as shown. Superheated coolant 262 is preferably further used in coolant use process 320 (see FIG. 6).

Figure 5:
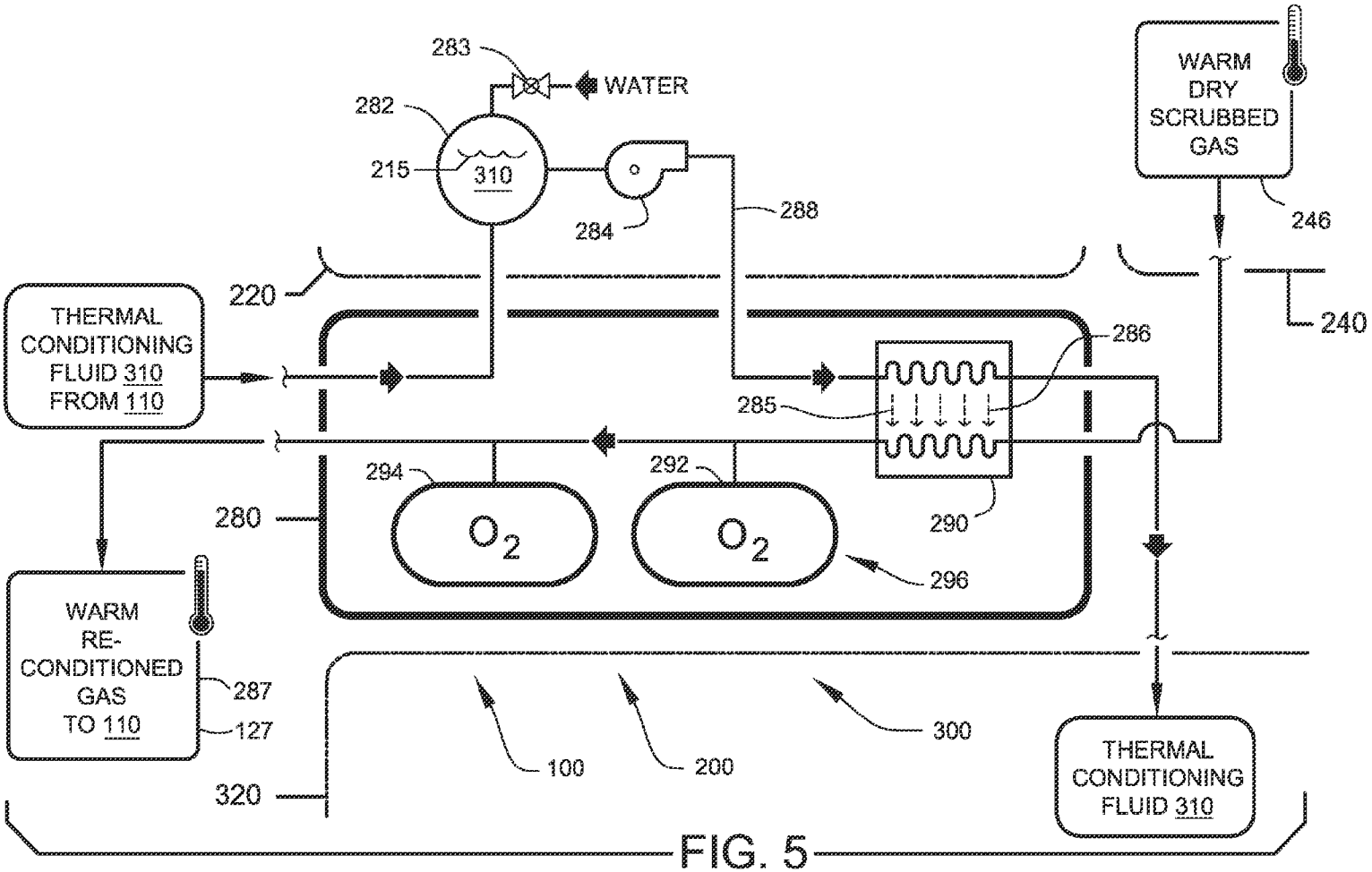
FIG. 5 shows a diagrammatic view, illustrating at least one resupply stage of the respiration conditioning cycle, according to the preferred embodiment of FIG. 1.

FIG. 5 shows a diagrammatic view, illustrating resupply stage 280 of respiration conditioning cycle 200, according to the preferred embodiment of FIG. 1. Resupply stage 280 preferably rehydrates, warms and resupplies oxygen to warmer dry scrubbed gas 246 making warmed reconditioned gas 287, as shown. Warmed reconditioned gas 287 comprises reconditioned gases 127 fed back to respiration chamber 120, as shown.

Warmer dry scrubbed gas 246, having been warmed in heat recuperation stage 240, is preferably further warmed and humidified, preferably in heat exchanger 290, as shown. At least one heat exchange 285 preferably is between warmer dry scrubbed gas 246 and thermal conditioning cycle 300, as shown. Heat exchange 285 (at least herein embodying wherein such at least one re-humidifier comprises at least one moisture returner adapted to return the captured moisture from such at least one moisture capture to such portions of such expired breath, assisting formation of warmed humidified such portions to include in such inspiration breath; and at least herein embodying wherein such re-humidifier means comprises moisture returning means for returning the captured moisture horn such moisture captures means to such portions of such expired breath to form warmed, humidified such portions for inclusion in such inspiration breath) preferably also allows humidification 286 of warmer dry scrubbed gas 246, as shown. Humidification 286 preferably proceeds at a water addition rate of about 60 grams/hour. Warmer dry scrubbed gas 246, through heat exchange 285 (at least embodying herein at least one inspiration-breath warmer adapted to warm such portions of such expired breath prior to inspiration; and at least embodying herein inspiration-breath warming means for warming such portions of such expired breath prior to inspiration; and at least embodying herein warming such portions of such expired breath prior to inspiration), receives heat and humidity from thermal conditioning cycle 300, as shown, becoming warmed rehydrated gas 298.

Water 215 from water extraction stage 220 is preferably recycled into thermal conditioning cycle 300, preferably using feedwater accumulator 282, as shown. Check valve 283 preferably prevents back flow of water 215 into feed line 288, as shown. Circulation pump 284 preferably maintains circulation of thermal conditioning fluid 310 in thermal conditioning cycle 300, preferably including through heat exchanger 290, as shown. At least one oxygen subsystem 296 preferably resupplies oxygen into warmed rehydrated gas 298, in respiration conditioning loop 201 (at least embodying herein at least one breathable gas mixer adapted to mix breathable gas from such at least one breathable gas storer with such warmed humidified portions; and at least embodying herein mixing such breathable gas with such warmed humidified portions prior to inspiration), to form warmed reconditioned gas 287, as shown. Oxygen subsystem 296 preferably comprises at least one primary oxygen subsystem 294 and at least one secondary oxygen subsystem 292, as shown. After oxygen is replenished by oxygen subsystem 296 (at least embodying herein at least one breathable gas storer adapted to store breathable gas; and at least embodying herein storing breathable gas), temperature of warmed reconditioned gas 287 entering contained environment 110 preferably comprises between about 277 K ("K" is the International System of Units ("SI") symbol for a unit increment of temperature on the Kelvin scale) and about 305 K, with a dew point preferably comprising between about 272 K and about 283 K.

Figure 6:
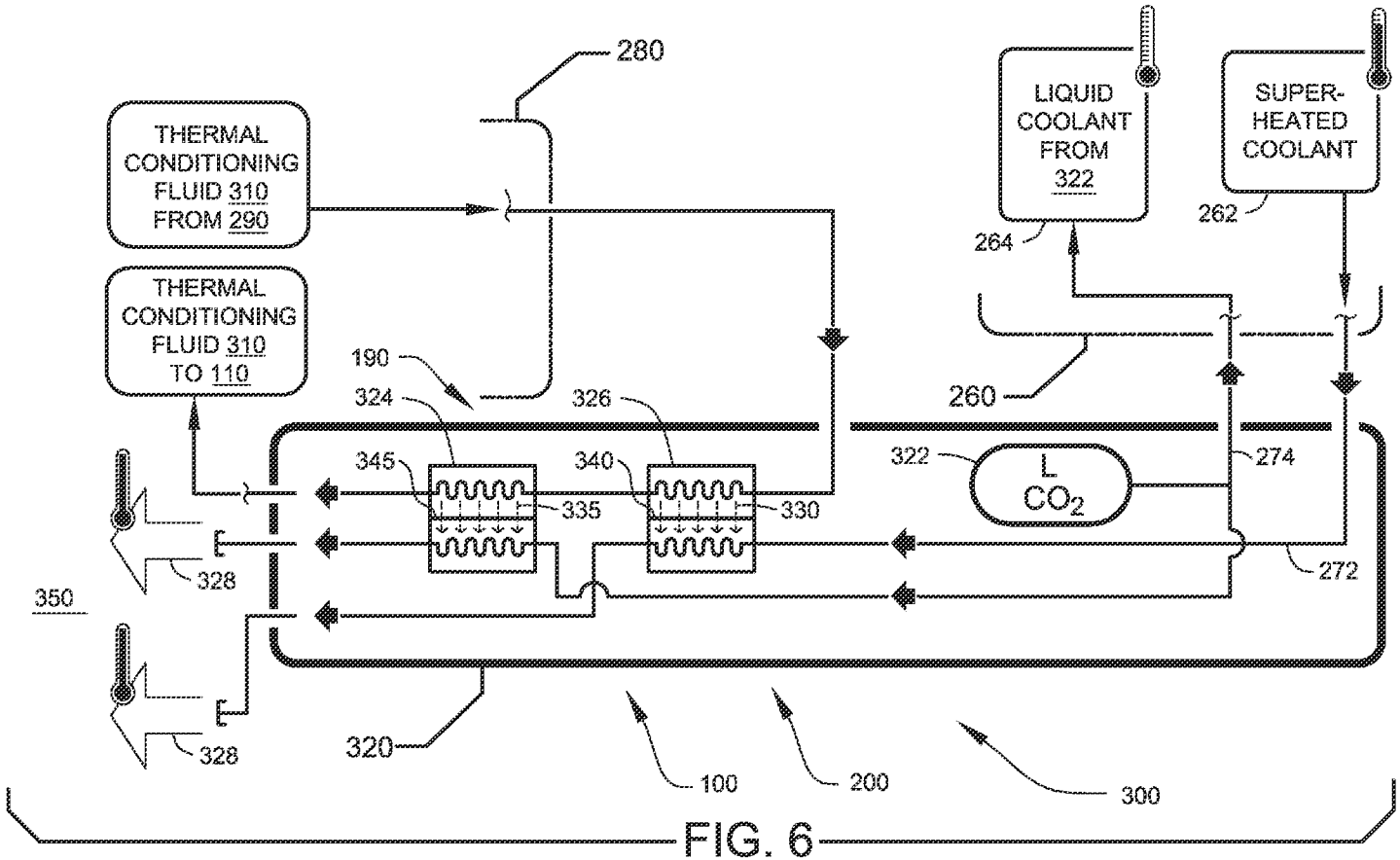
FIG. 6 shows a diagrammatic view, illustrating at least one coolant use process of the environmental conditioning cycle, according to the preferred embodiment of FIG. 1.

FIG. 6 shows a diagrammatic view, illustrating at least one coolant use process 320 of environmental conditioning cycle 190, according to the preferred embodiment of FIG. 1. In embodiment 102, liquid coolant 264 preferably comprises liquid carbon dioxide, as shown. Liquid coolant 264 is preferably stored in at least one liquid coolant supply 322, as shown. Upon reading the teachings of this specification, those skilled in the art will now appreciate that, under appropriate circumstances, considering such issues as future technology, cost, external environments, etc., other coolants, such as, for example, methane, oxygen, helium, glycerine, etc., may suffice.

Liquid coolant 264 preferably feeds, as shown, to gas scrubbing stage 260 in order to cool sorbent bed 236 as described in FIG. 4. Superheated coolant 262 preferably returns from gas scrubbing stage 260 in coolant feed line 272, as shown.

Superheated coolant 262 preferably passes through at least one heat exchanger 326, preferably to use any remaining cooling power, prior to being exhausted to external environment 350, as shown. Liquid coolant 264 preferably additionally directly feeds at least one heat exchanger 324, as needed by thermal conditioning cycle 300.

Thermal conditioning cycle 300 preferably utilizes heat exchanger 290, heat exchanger 326 and heat exchanger 324 (at least embodying herein at least one suit cooler adapted to cool body-heat suit warming; and at least embodying herein cooling body-heat warming such at least one extraterrestrial suit), preferably to maintain temperature of thermally regulated chamber 150, as shown. Heat exchanger 326 preferably comprises heat exchange 330 across at least one gas impermeable barrier 340, as shown. Likewise, Heat exchanger 324 preferably comprises heat exchange 335 across at least one gas impermeable barrier 345, as shown.

Heat exchanger 290 (shown in FIG. 5) preferably allows recycling of heat from thermal conditioning cycle 300 prior to using liquid coolant 264 and superheated coolant 262, as shown. Next, heat exchange 330 preferably further uses superheated coolant 262 for further cooling of thermal conditioning fluid 310, as shown. Only when further cooling is needed, heat exchange 335 preferably uses liquid coolant 264 to cool thermal conditioning fluid, as shown. Heat exchange 330 and heat exchange 335 (at least herein embodying wherein such at least one suit cooler comprises such liquid carbon dioxide; and at least herein embodying wherein such cooling utilizes such liquid carbon dioxide) preferably form hot waste coolant 328, which is preferably exhausted to environment 350, as shown. Upon reading the teachings of this specification, those skilled in the art will now appreciate that, under appropriate circumstances, considering such issues as future technology, cost, environmental limitations, etc., other heat exchanges for thermal conditioning, such as, for example, thermo-electric, chemical reactions, etc., may suffice.

Coolant-superheating heat exchange 275, sublimation heat exchange 265, heat exchange 330 and heat exchange 335 preferably use gas impermeable barriers to prevent contamination of hot waste coolant 328, where hot waste coolant 328 exhausts to external environment 350.

Figure 7A:
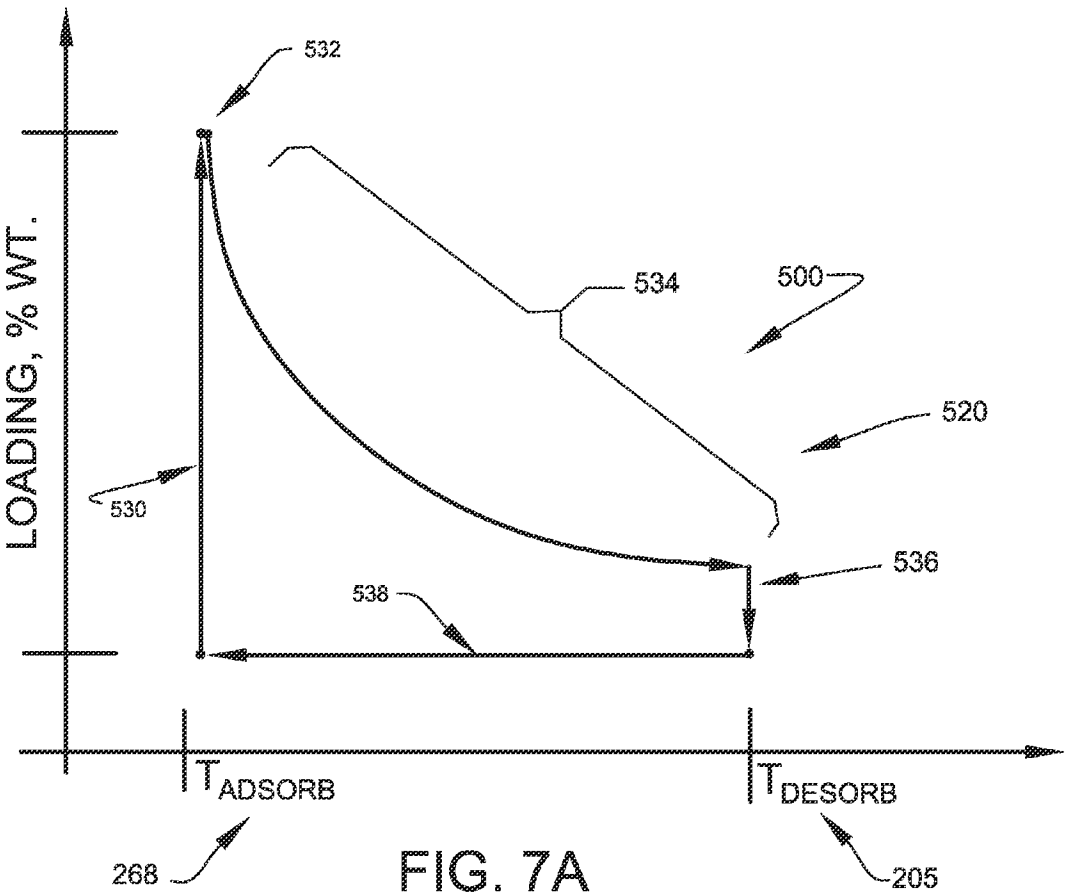
FIG. 7A shows a graph view, illustrating a thermodynamic loading cycle of at least one sorbent bed, according to the preferred embodiment of FIG. 1.

FIG. 7A shows a graph view, illustrating at least one thermodynamic loading cycle 500 of sorbent bed 236, according to the preferred embodiment of FIG. 1. Thermodynamic loading cycle 500 preferably comprises, as shown, at least one sorbent bed cooling 538, at least one adsorption 530, at least one adsorption to desorption changeover 532, at least one warming 534, and at least one final desorption 536.

Sorbent bed cooling 538 preferably comprises cooling sorbent bed 236, using liquid coolant 264, from desorption temperature 205 to adsorption temperature 268, as shown. In embodiment 102, desorption temperature 205 preferably comprises between about 270 K and about 280 K, preferably about 280 K. Additionally, adsorption temperature 268 preferably comprises between about 210 K and about 215 K, preferably about 210 K. Temperature of liquid coolant 264 comprises about 195 K. Upon reading the teachings of this specification, those skilled in the art will now appreciate that, under appropriate circumstances, considering such issues as future technology, cost, future materials, etc., other adsorption and desorption temperatures may suffice.

Once reaching adsorption temperature 268, adsorption 530 begins, as shown. Adsorption 530 preferably comprises removal of carbon dioxide from cool dry carbon-dioxide-laden gas 242. Adsorption 530 comprises an exothermic reaction bonding carbon dioxide to sorbent bed 236. Excess heat generated by exothermic reaction preferably transfers out of sorbent bed 236 in sublimation heat exchange 265. Adsorption 530 preferably continues until sorbent bed 236 is fully loaded. Applicant has determined, through testing and modeling, that adsorption 530 takes about 6 minutes.

After sorbent bed 236 becomes loaded, sorbent bed 236 preferably switches to desorption mode in adsorption to desorption changeover 532, as shown. During adsorption to desorption changeover 532, system pressure drops to ambient pressure of external environment 350. When external environment 350 comprises Mars, such ambient pressure preferably comprises carbon dioxide partial pressure of about 0.8 kPa (kilopascal).

After adsorption to desorption changeover 532, sorbent bed 236 preferably warms to desorption temperature 205 using heat exchange 227 (shown as sorbent bed warming 534). Warm moist carbon-dioxide-laden gases 225 used in heat exchange 227 preferably comprises a temperature of about 300 K. Desorption 520 comprises an endothermic reaction, such that during warming 534 desorption 520 preferably begins before desorption temperature 205 is reached. Once desorption temperature 205 is reached, final desorption 536 completes desorption 520 of carbon dioxide from sorbent bed 236, as shown. Applicant has determined, through modeling and testing that desorption comprises about 6 minutes.

After final desorption 536, thermodynamic loading cycle 500 begins again. Upon reading the teachings of this specification, those skilled in the art will now appreciate that, under appropriate circumstances, considering such issues as future technology, cost, environmental limitations, etc., other thermodynamic cycles may suffice.

Figure 7B:
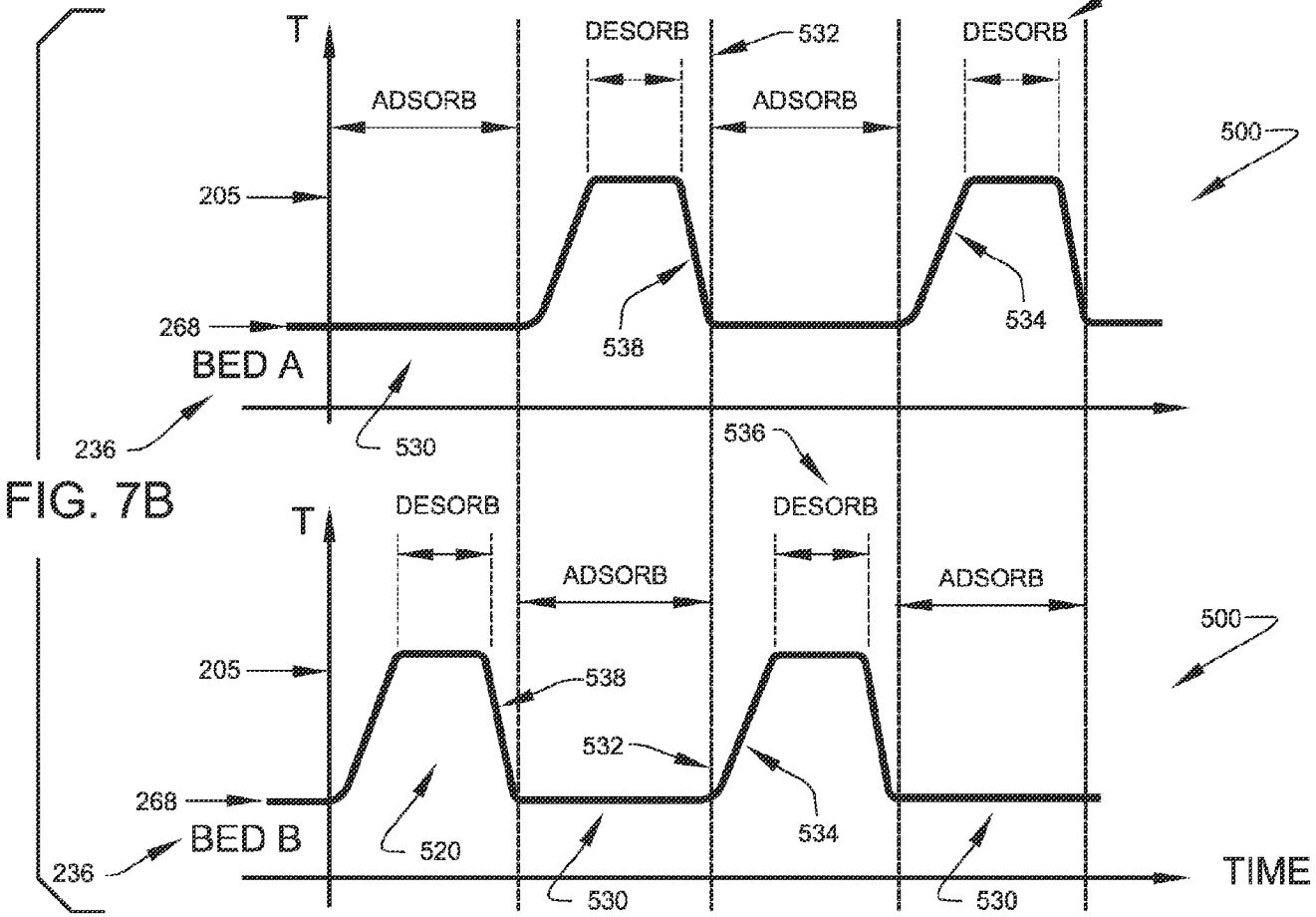
FIG. 7B shows a graph view, illustrating at least two sorbent beds each following the thermodynamic loading cycle, according to the preferred embodiment of FIG. 7A.

FIG. 7B shows a graph view, illustrating two sorbent beds 236 each following thermodynamic loading cycle 500, according to the preferred embodiment of FIG. 7A. Two sorbent beds 236 (identified herein as Bed A and Bed B) preferably alternate between adsorption 530 and desorption 520 in thermodynamic loading cycle 500. Sorbent beds 236 preferably alternate modes in thermodynamic loading cycle 500 such that sorbent beds 236 are consistently in opposite modes of operation, in a time-phase shift, as shown. By so time-phase shifting thermodynamic loading cycle 500 in different sorbent beds 236, one sorbent bed 236, comprising desorbing MTSA module 231, will be exhausting carbon dioxide gas 237 to external environment 350, while one sorbent bed 236, comprising adsorbing MTSA module 233, absorbs more carbon dioxide from respiration conditioning cycle 200. Thus, a substantially continuous removal of carbon dioxide may preferably be maintained.

Figure 8:
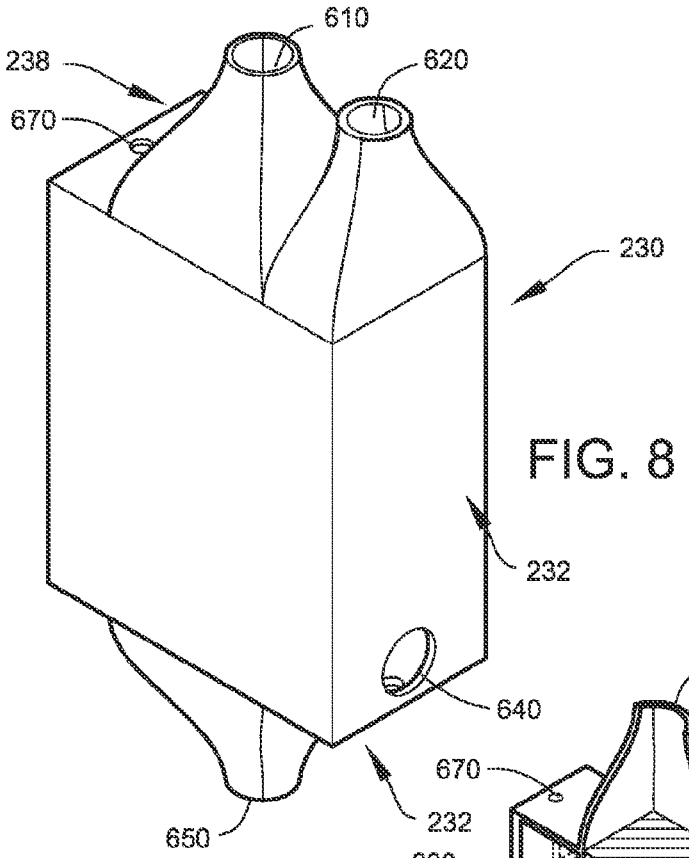
FIG. 8 shows a perspective view, illustrating a metabolic heat regenerated temperature swing adsorption module of the respiration conditioning cycle, according to the preferred embodiment of FIG. 1.

FIG. 8 shows a perspective view, illustrating metabolic heat regenerated temperature swing adsorption module 230 of respiration conditioning cycle 200, according to the preferred embodiment of FIG. 1.

Figure 9:
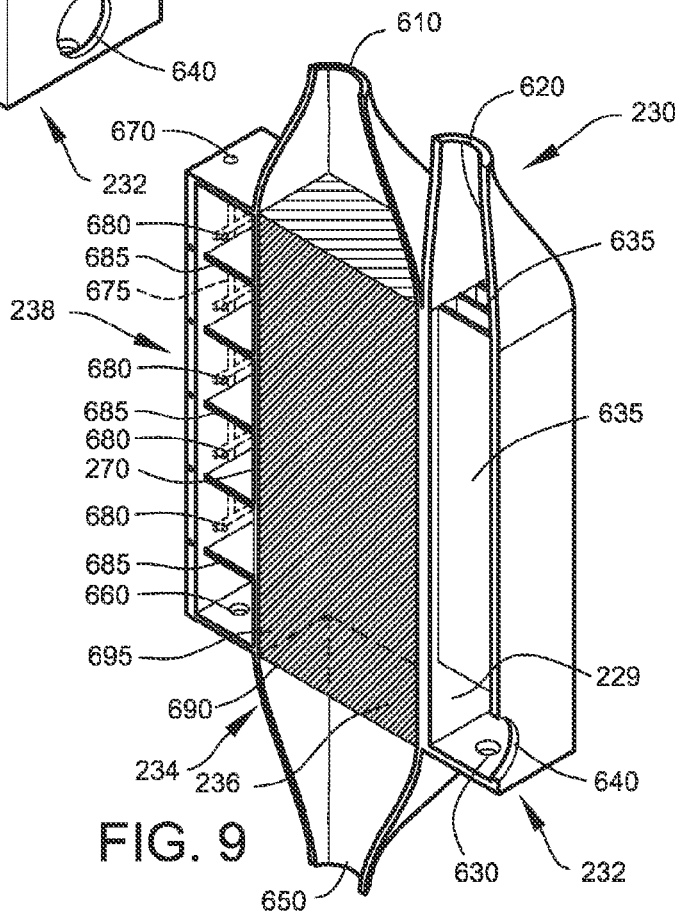
FIG. 9 shows a perspective cutaway view, illustrating a sorbent bed of the metabolic heat regenerated temperature swing adsorption module of the respiration conditioning cycle, according to the preferred embodiment of FIG. 8.

FIG. 9 shows a perspective cutaway view, illustrating a sorbent bed 236 of metabolic heat regenerated temperature swing adsorption module 230 of respiration conditioning cycle 200, according to the preferred embodiment of FIG. 8. Referring to FIG. 8 and FIG. 9 together, metabolic heat regenerated temperature swing adsorption module 230 preferably comprises, as shown, sorbent-bed chamber 234, heat exchanger 232 and heat exchanger 238, as discussed in FIG. 2.

Sorbent-bed chamber 234, heat exchanger 232 and heat exchanger 238 are preferably joined adjacent, as shown. Non-gas-permeable barrier 270 preferably comprises at least one shared wall between sorbent-bed chamber 234 and heat exchanger 238, as shown. Further, gas impermeable barrier 229 (at least embodying herein at least one thermal conductor adapted to assist thermal conductivity between such expired breath and such at least one expiration-breath cooler; and at least embodying herein thermal conductor means for assisting thermal conductivity between such expired breath and such expiration-breath cooler means; and at least embodying herein assisting thermal conductivity between such expired breath and such at least one expired-breath cooler) preferably comprises at least one other shared wall between sorbent-bed chamber 234 and heat exchanger 232, as shown. Upon reading the teachings of this specification, those skilled in the art will now appreciate that, under appropriate circumstances, considering such issues as future technology, cost, heat transfer optimizations, etc., other geometries, such as, for example, cylindrical, interwoven, helical, etc., may suffice.

During desorption 520, heat exchanger 232 preferably allows gasses to pass through heat exchanger 232 from gas entrance port 620 across at least one condenser fin 635 to gas exit port 640.

Condenser fin 635 preferably transfers heat from such gasses to sorbent-bed chamber 234, while also collecting water via condensation. Ice preferably forms on condenser fin 635 while temperatures are below freezing; however, as sorbent bed 236 warms from heat exchange 227. Such ice melts and exits heat exchanger 232 through at least one drain port 630, as shown. Drain port preferably connects to feed line 288, as shown in FIG. 2.

During adsorption 530, liquid coolant 264 enters heat exchanger 238 through at least one coolant inlet 670. Coolant inlet 670 preferably connects to at least one distribution channel 675 that in turn connects to at least one chamber distribution port 680, as shown. Liquid coolant 264 preferably distributes across heat exchanger 238 and preferably solidifies. At least one heat transfer fin 685 preferably transfers heat from sorbent-bed chamber 234 into solidified coolant causing sublimation into coolant vapor. Such coolant vapor expands into heat exchanger 238 drawing further heat in coolant-superheating heat exchange 275 forming superheated coolant 262. Superheated coolant 262 preferably exits heat exchanger 238 through coolant outlet port 660.

Also during adsorption 530, cool dry carbon-dioxide-laden gas 242 preferably enters adsorbing MTSA module 233 through inlet port 610. Cool dry carbon-dioxide-laden gas 242 (at least herein embodying wherein such at least one expiration-breath cooler comprises such cooled, de-humidified expired breath) is cooled using heat exchange 275 to adsorption temperature 268, then sorbent 695 adsorbs carbon dioxide from cool dry carbon-dioxide-laden gas 242 using heat exchange 265. Exiting sorbent-bed chamber 234, using outlet port 650, preferably is cold dry scrubbed gas 244.

Sorbent-bed chamber 234 preferably contains sorbent bed 236, as shown. Sorbent bed 236 preferably comprises dimensions of about two inches by about two inches by about five inches. Square cross-section of sorbent bed 236 preferably reduces thermal mass of sorbent-bed chamber 234, preferably requiring less heat for warming to desorption temperature 205. Upon reading the teachings of this specification, those skilled in the art will now appreciate that, under appropriate circumstances, considering such issues as future technology, cost, environmental limitations, etc., other dimensions may suffice.

Sorbent bed 236 preferably comprises at least one foam base 690, as shown, preferably comprising aluminum foam, preferably 6061-T6 aluminum foam, preferably 8% density aluminum foam. Foam base preferably comprises about 40 PPI (pores per inch). Upon reading the teachings of this specification, those skilled in the art will now appreciate that, under appropriate circumstances, considering such issues as future technology, cost, cycle time requirements, etc., other foams, such as, for example, denser foams, less dense foams, non-aluminum foams, etc., may suffice.

Foam base 690 is preferably dip brazed into sorbent-bed chamber 234, as shown. Upon reading the teachings of this specification, those skilled in the art will now appreciate that, under appropriate circumstances, considering such issues as future technology, cost, thermal requirements, etc., other mountings, such as, for example, thermal epoxies, inserted holders, etc., may suffice.

Foam base 690 preferably is washcoated with at least one sorbent 695, as shown, using current techniques and parameters as established by PCI (Precision Combustion, Inc. of North Haven, Conn.). Upon reacting the teachings of this specification, those skilled in the art will now appreciate that, under appropriate circumstances, considering such issues as future technology, cost, materials, etc., other coating methods, such as, for example, dip coating, plating, spray coating, etc., may suffice.

Sorbent 695 (at least herein embodying wherein such at least one carbon dioxide adsorber comprises at least one sorbent adapted to adsorb and/or desorb carbon dioxide, the mode correlating with temperature of such at least one sorbent; and at least herein embodying wherein such adsorbing utilizes at least one sorbent adapted to adsorb and/or desorb carbon dioxide, the mode correlating with temperature of such at least one sorbent) preferably comprises NaX zeolite. Upon reading the teachings of this specification, those skilled in the art will now appreciate that, under appropriate circumstances, considering such issues as future technology, cost, materials, etc., other sorbents, such as, for example, activated charcoal, metallic sorbents, etc., may suffice.

Upon reading the teachings of this specification, those skilled in the art will now appreciate that, under appropriate circumstances, considering such issues as future technology, cost, system requirements, etc., other sorbent geometries, such as, for example, balls, plates, screens, membranes, etc., may suffice.

Metabolic heat regenerated temperature swing adsorption module 230 preferably comprises metal, preferably aluminum, preferably 6061-T6 aluminum. Upon reading the teachings of this specification, those skilled in the art will now appreciate that, under appropriate circumstances, considering such issues as future technology, cost, thermal transfer requirements, etc., other materials, such as, for example, other metals, cermets, plastics, etc., may suffice.

Sorbent-bed chamber 234 is preferably made from a square tube comprising about two inches on a side, having a wall thickness of about 0.05 inches, as shown. Upon reading the teachings of this specification, those skilled in the art will now appreciate that, under appropriate circumstances, considering such issues as future technology, cost, thermal transfer requirements, etc., other sorbent chamber geometries, such as, for example, cylindrical, cubic, ridged, etc., may suffice.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A system, relating to human respiration in extraterrestrial environments, comprising:

[a)] at least one expiration-breath holder adapted to hold expired breath;

[b)] at least one expiration-breath cooler adapted to cool the expired breath;

[c)] at least one gas-impermeable separator adapted to separate said at least one expiration-breath holder from said at least one expiration-breath cooler;

[d)] at least one thermal conductor adapted to assist thermal conductivity between such expired breath and said at least one expiration-breath cooler; [and]

[e)] wherein said at least one expiration-breath holder comprises at least one moisture capturer adapted to capture moisture from such expired breath as such expired breath is cooled by said at least one expiration-breath cooler, assisting formation of cooled, de-humidified expired breath;

[f) at least one moisture holder adapted to hold moisture captured by said at least one moisture capturer;]

[g)] at least one inspiration-breath holder adapted to hold portions of such expired breath desired to be included in inspiration breath;

[h)] at least one inspiration-breath warmer adapted to warm such portions of such expired breath prior to inspiration; [and]

[i)] at least one re-humidifier adapted to re-humidify such portions of such expired breath;

[j)] wherein said at least one re-humidifier comprises at least one moisture returner adapted to return the captured moisture from said at least one moisture capture to such portions of such expired breath, assisting formation of warmed humidified such portions to include in such inspiration breath;

[k)] at least one carbon dioxide adsorber adapted to adsorb carbon dioxide from such cooled, de-humidified expired breath;

[l)] at least one further cooler adapted to further cool such cooled, de-humidified expired breath;

[m)] at least one extraterrestrial body suit adapted to extraterrestrial body protection; and

[n)] at least one suit cooler adapted to cool [body-heat suit warming] *said at least one extraterrestrial body suit*;

[o)] wherein said at least one further cooler comprises liquid carbon dioxide; [and]

[p)] wherein said at least one suit cooler comprises said liquid carbon dioxide.

2. The system according to claim 1 wherein said at least one expiration-breath cooler comprises such cooled, de-humidified expired breath.

3. The system according to claim 1 further comprising:

[a)] at least one breathable gas storer adapted to store breathable gas; and

[b)] at least one breathable gas mixer adapted to mix breathable gas from said at least one breathable gas storer with such warmed humidified portions.

4. The system according to claim 1 wherein said at least one carbon dioxide adsorber comprises at least one sorbent adapted to adsorb and/or desorb carbon dioxide, the mode correlating with temperature of said at least one sorbent.

5. The system according to claim 4 wherein said at least one sorbent comprises at least one desorber adapted to desorbing carbon dioxide into the environment to re-prepare said at least one sorbent for re-use as said carbon dioxide adsorber.

6. The system according to claim 5 wherein said desorber uses thermal transfer from warmth of such expired breath to attain at least one desorbing condition.

7. The system according to claim 1 wherein said at least one carbon dioxide adsorber comprises said liquid carbon dioxide.

8. The system according to claim 1 wherein [the body heat warming] said at least one extraterrestrial body suit assists providing the warmth to warm such inspiration breath *from body heat*.

9. A method, relating to human respiration in extraterrestrial environments, comprising the steps of:

[a)] collecting and holding expired breath;

[b)] cooling such expired breath using at least one expired-breath cooler;

[c) gas-impermeably separating such expired breath from such at least one expired-breath cooler;]

[d)] assisting thermal conductivity between such expired breath and such at least one expired-breath cooler;

[e)] capturing moisture from such expired breath as such expired breath is cooled by such at least one expired-breath cooler, assisting formation of cooled, de-humidified expired breath;

[f) holding such captured moisture;]

[g)] holding portions of such expired breath desired to be included in inspiration breath;

[h)] warming such portions of such expired breath prior to inspiration;

[i)] re-humidifying, with such captured moisture, such portions of such expired breath to form warmed humidified such portions to include in such inspiration breath;

[j)] adsorbing carbon dioxide from such cooled, de-humidified expired breath; [and]

[k)] further cooling such cooled, de-humidified expired breath;

[l)] wherein such further cooling utilizes liquid carbon dioxide;

[m)] protecting at least one body in at least one extraterrestrial suit; and

[n)] cooling [body-heat warming] such at least one extraterrestrial suit;

[o)] wherein such cooling utilizes such liquid carbon dioxide.

10. The method according to claim 9 wherein such at least one expired-breath cooler comprises such cooled, de-humidified expired breath.

11. The method according to claim 9 further comprising the steps of:

[a)] storing breathable gas; and

[b)] mixing such breathable gas with such warmed humidified portions prior to inspiration.

12. The method according to claim 9 wherein such adsorbing utilizes at least one sorbent adapted to adsorb and/or desorb carbon dioxide, the mode correlating with temperature of such at least one sorbent.

13. The method according to claim 12 further comprising desorbing carbon dioxide into the environment to re-prepare such at least one sorbent for re-use in such adsorbing.

14. The method according to claim 13 wherein such desorbing utilizes thermal transfer from warmth of such expired breath to attain at least one desorbing condition.

15. The method according to claim 9 wherein such adsorbing utilizes such liquid carbon dioxide.

16. A system, relating to human respiration in extraterrestrial environments, comprising:

[a)] at least one expiration-breath holder adapted to hold expired breath;

[b)] at least one expiration-breath cooler adapted to cool the expired breath;

[c)] at least one gas-impermeable separator adapted to separate said at least one expiration-breath holder from said at least one expiration-breath cooler;

[d)] at least one thermal conductor adapted to assist thermal conductivity between such expired breath and said at least one expiration-breath cooler; [and]

[e)] wherein said at least one expiration-breath holder comprises at least one moisture capturer adapted to capture moisture from such expired breath as such expired breath is cooled by said at least one expiration-breath cooler, assisting formation of cooled, de-humidified expired breath;

[f) at least one moisture holder adapted to hold moisture captured by said at least one moisture capturer;]

[g)] at least one inspiration-breath holder adapted to hold portions of such expired breath desired to be included in inspiration breath;

[h)] at least one inspiration-breath warmer adapted to warm such portions of such expired breath prior to inspiration;

[i)] at least one re-humidifier adapted to re-humidify such portions of such expired breath; and

[j)] at least one carbon dioxide adsorber adapted to adsorb carbon dioxide from such cooled, de-humidified expired breath;

[k)] wherein said at least one carbon dioxide adsorber comprises at least one sorbent adapted to adsorb and/or desorb carbon dioxide, the mode correlating with temperature of said at least one sorbent;

[l)] wherein said at least one re-humidifier comprises at least one moisture returner adapted to return the captured moisture from said at least one moisture capture to such portions of such expired breath, assisting formation of warmed humidified such portions to include in such inspiration breath;

[m)] wherein said at least one sorbent comprises at least one desorber adapted to desorbing carbon dioxide into the environment to re-prepare said at least one sorbent for re-use as said carbon dioxide adsorber; and

[n)] wherein said desorber uses thermal transfer from warmth of such expired breath to attain at least one desorbing condition.

17. The system according to claim 16 wherein said at least one expiration-breath cooler comprises such cooled, de-humidified expired breath.

18. The system according to claim 16 further comprising:

[a)] at least one breathable gas storer adapted to store breathable gas; and

[b)] at least one breathable gas mixer adapted to mix breathable gas from said at least one breathable gas storer with such warmed humidified portions.

19. The system according to claim 16 further comprising at least one further cooler adapted to further cool such cooled, de-humidified expired breath.

20. The system according to claim 19 wherein said at least one further cooler comprises liquid carbon dioxide.

21. The system according to claim 20 wherein said *at least one carbon dioxide absorber comprises said* liquid carbon dioxide [comprises said at least one carbon dioxide adsorber].

22. The system according to claim 20 further comprising:

[a)] at least one extraterrestrial body suit adapted to extraterrestrial body protection; and

[b)] at least one suit cooler adapted to cool [body-heat suit warming] *said at least one extraterrestrial body suit*;

[c)] wherein said at least one suit cooler comprises said liquid carbon dioxide.

23. The system according to claim 22 wherein [the body heat warming] said at least one extraterrestrial body suit assists providing the warmth to warm such inspiration breath *from body heat*.

24. A method, relating to human respiration in extraterrestrial environments, comprising the steps of:

[a)] collecting and holding expired breath;

[b)] cooling such expired breath using at least one expired-breath cooler;

[c) gas-impermeably separating such expired breath from such at least one expired-breath cooler;]

[d)] assisting thermal conductivity between such expired breath and such at least one expired-breath cooler;

[e)] capturing moisture from such expired breath as such expired breath is cooled by such at least one expired-breath cooler, assisting formation of cooled, de-humidified expired breath;

[f) holding such captured moisture;]

[g)] holding portions of such expired breath desired to be included in inspiration breath;

[h)] warming such portions of such expired breath prior to inspiration;

[i)] re-humidifying, with such captured moisture, such portions of such expired breath to form warmed humidified such portions to include in such inspiration breath;

[j)] adsorbing carbon dioxide from such cooled, de-humidified expired breath; and

[k)] desorbing carbon dioxide into the environment to re-prepare such at least one sorbent for re-use in such adsorbing;

[l)] wherein such adsorbing utilizes at least one sorbent adapted to adsorb and/or desorb carbon dioxide, the mode correlating with temperature of such at least one sorbent; and

[m)] wherein such desorbing utilizes thermal transfer from warmth of such expired breath to attain at least one desorbing condition.

25. The method according to claim 24 wherein such at least one expired-breath cooler comprises such cooled, de-humidified expired breath.

26. The method according to claim 24 further comprising the steps of:

[a)] storing breathable gas; and

[b)] mixing such breathable gas with such warmed humidified portions prior to inspiration.

27. The method according to claim 24 further comprising further cooling such cooled, de-humidified expired breath.

28. The method according to claim 27 wherein such further cooling utilizes liquid carbon dioxide.

29. The method according to claim 28 wherein such adsorbing utilizes such liquid carbon dioxide.

30. The method according to claim 28 further comprising:

[a)] protecting at least one body in at least one extraterrestrial suit; and

[b)] cooling [body-heat warming] such at least one extraterrestrial suit;

[c)] wherein such cooling utilizes such liquid carbon dioxide.

*31. A system comprising:*

*at least one metabolic heat regenerated temperature swing adsorption (MTSA) module, the at least one MTSA module configured to receive expired breath from a person, wherein the at least one MTSA module includes:*

*at least one sorbent, the at least one sorbent configured to adsorb carbon dioxide at an adsorption temperature and desorb carbon dioxide at a desorption temperature;*

*at least one heat exchanger, wherein the at least one sorbent is configured to desorb carbon dioxide at the desorbing temperature via the at least one heat exchanger, the at least one heat exchanger transfer-*

*ring warmth from the expired breath to attain the desorbing temperature and produce cooled expired breath from the expired breath, wherein the at least one sorbent is further configured to adsorb carbon dioxide from the cooled expired breath at the adsorbing temperature and produce cold scrubbed gas from the cooled expired breath.*

*32. The system of claim 31, wherein the desorption temperature is between about 270 K and about 280 K, and the adsorption temperature is between about 210 K and about 215 K.*

*33. The system of claim 31, wherein the at least one MTSA module comprises a first MTSA module and a second MTSA module, the first MTSA module including a first sorbent and a first heat exchanger, and the second MTSA module including a second sorbent and a second heat exchanger, wherein the first sorbent is configured to adsorb carbon dioxide when the second sorbent desorbs carbon dioxide via the second heat exchanger, and wherein the first sorbent is configured to desorb carbon dioxide via the first heat exchanger when the second sorbent adsorbs carbon dioxide.*

*34. The system of claim 31, further comprising:*

*a coolant including liquid carbon dioxide, the at least one heat exchanger configured to heat the coolant during adsorption of carbon dioxide from the expired breath.*

*35. The system of claim 34, wherein the coolant is configured to further cool the cooled expired breath to produce the cold scrubbed gas.*

*36. The system of claim 34, further comprising:*

*an extraterrestrial body suit adapted to extraterrestrial body protection of the person; and*

*at least one additional heat exchanger, wherein the coolant is further configured to cool the extraterrestrial body suit via the at the at least one additional heat exchanger.*

*37. The system of claim 31, wherein the at least one heat exchanger includes one or more gas impermeable barriers.*

*38. The system of claim 31, further comprising:*

*a moisture capturer configured to capture moisture from the expired breath when the at least one sorbent desorbs carbon dioxide via the at least one heat exchanger.*

*39. The system of claim 38, further comprising:*

*a humidifier coupled to the moisture capturer and configured to humidify the cold scrubbed gas with the captured moisture to produce rehydrated gas.*

*40. The system of claim 39, further comprising:*

*at least one additional heat exchanger, the at least one additional heat exchanger configured to warm the rehydrated gas to produce warm, rehydrated gas.*

*41. The system of claim 31, wherein the at least one sorbent is configured to desorb carbon dioxide at ambient pressure.*

*42. The system of claim 41, wherein the ambient pressure includes a partial pressure of carbon dioxide about equal to or greater than 0.8 kPa.*

*43. The system of claim 31, wherein the at least one sorbent includes NaX zeolite.*

*44. A method comprising:*

*providing expired breath from a person to at least one metabolic heat regenerated temperature swing adsorption (MTSA) module, wherein the at least one MTSA module includes at least one sorbent and at least one heat exchanger;*

*transferring warmth from the expired breath to the at least one sorbent to attain a desorbing temperature via the at least one heat exchanger;*

*desorbing carbon dioxide to an environment outside the at least one MTSA module at the desorbing temperature;*

*cooling the expired breath to form cooled expired breath via the at least one heat exchanger;*

*providing the cooled expired breath to the at least one MTSA module; and*

*adsorbing carbon dioxide in the at least one sorbent from the cooled expired breath at an adsorbing temperature to produce cold scrubbed gas.*

*45. The method of claim 44, wherein the desorption temperature is between about 270 K and about 280 K, and the adsorption temperature is between about 210 K and about 215 K.*

*46. The method of claim 44, wherein the at least one MTSA module comprises a first MTSA module and a second MTSA module, the first MTSA module including a first sorbent and a first heat exchanger, and the second MTSA module including a second sorbent and a second heat exchanger, and wherein desorbing carbon dioxide occurs in the first MTSA module when adsorbing carbon dioxide occurs in the second MTSA module, and wherein desorbing carbon dioxide occurs in the second MTSA module when adsorbing carbon dioxide occurs in the first MTSA module.*

*47. The method of claim 44, further comprising:*

*cooling further the cooled expired breath to produce the cold scrubbed gas using a coolant including liquid carbon dioxide; and*

*heating the coolant including liquid carbon dioxide via the at least one heat exchanger during adsorption of carbon dioxide from the expired breath.*

*48. The method of claim 44, further comprising:*

*capturing moisture from the expired breath during cooling of the expired breath.*

*49. The method of claim 48, further comprising:*

*humidifying the cold scrubbed gas with the captured moisture; and*

*forming rehydrated gas.*

* * * * *